United States Patent
Constandse et al.

(10) Patent No.: US 11,913,062 B2
(45) Date of Patent: Feb. 27, 2024

(54) SYSTEM AND METHOD FOR ISOLATION AND QUALIFICATION OF NUCLEIC ACIDS

(71) Applicant: Roche Sequencing Solutions, Inc., Pleasanton, CA (US)

(72) Inventors: Victoria Constandse, Cape Town (ZA); Daniel Klass, Livermore, CA (US); Alexander Lovejoy, Newark, CA (US); Melissa Loyzer, Hamilton (CA); Bronwen Miller, Cape Town (ZA); Bernd Hinzmann, Berlin (DE); Sophie Beckert, Neuzelle (DE)

(73) Assignees: Roche Sequencing Solutions, Inc., Pleasanton, CA (US); Signature Diagnostics GmbH, Potsdam (DE)

( * ) Notice: Subject to any disclaimer, the term of this patent is extended or adjusted under 35 U.S.C. 154(b) by 1047 days.

(21) Appl. No.: 16/687,274

(22) Filed: Nov. 18, 2019

(65) Prior Publication Data
US 2020/0087708 A1    Mar. 19, 2020

Related U.S. Application Data

(63) Continuation of application No. PCT/US2018/033279, filed on May 17, 2018.
(Continued)

(51) Int. Cl.
*C12Q 1/68* (2018.01)
*C12Q 1/6806* (2018.01)
(Continued)

(52) U.S. Cl.
CPC ............ *C12Q 1/6806* (2013.01); *C40B 20/08* (2013.01); *C40B 30/10* (2013.01); *C40B 60/06* (2013.01); *G16B 40/10* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 2013/0137582 A1 | 5/2013 | Ong et al. | |
| 2016/0186239 A1* | 6/2016 | Sinha | C12Q 1/6851 506/9 |
| 2018/0288982 A1* | 10/2018 | Sinha | C12Q 1/6809 |
| 2020/0041489 A1* | 2/2020 | Emmert-Buck | C12Q 1/6841 |

FOREIGN PATENT DOCUMENTS

| | | |
|---|---|---|
| WO | 9820166 | 5/1998 |
| WO | WO2010026256 A1 | 3/2010 |

(Continued)

OTHER PUBLICATIONS

Kapabiosystems: Technical Data Sheet, KAPA Human Genomic DNA Quantification and QC Kit Contents, Oct. 1, 2016, avail at https://rochesequencingstore.com/wp-content/uploads/2017/10/KAPA-Human-Genomic-DNA-Quantification_QC-Kit-1.pdf.*
(Continued)

*Primary Examiner* — Aaron A Priest
(74) *Attorney, Agent, or Firm* — Eric Grant Lee

(57) ABSTRACT

Present disclosure provides a method including isolating DNA from a source, thereby providing a composition including the isolated DNA. The isolated DNA has at least first and second target regions, where the length of the second target region is greater than the length of the first target region. The method further includes quantifying a total mass of the isolated DNA, quantifying a first quantification cycle ($C_q$) of the first target region and a second $C_q$ of the second target region, and calculating a Q-ratio for the isolated DNA by dividing the second $C_q$ by the first $C_q$. The method further includes determining a value for a quality-mass constant ($k_{Qm}$), estimating a required input mass by dividing $k_{Qm}$ by the Q-ratio, and preparing the isolated DNA
(Continued)

for sequencing if the total mass of the isolated DNA in the composition is equal or greater than the required input mass.

2 Claims, 5 Drawing Sheets

Specification includes a Sequence Listing.

Related U.S. Application Data

(60) Provisional application No. 62/507,501, filed on May 17, 2017.

(51) Int. Cl.
    *C40B 20/08*     (2006.01)
    *C40B 30/10*     (2006.01)
    *C40B 60/06*     (2006.01)
    *G16B 40/10*     (2019.01)
    *G16B 30/00*     (2019.01)

(56) References Cited

FOREIGN PATENT DOCUMENTS

| | | |
|---|---|---|
| WO | 2012038503 A1 | 3/2012 |
| WO | WO2016183100 A1 | 11/2016 |

OTHER PUBLICATIONS (Sanders, R) Precision in RNA molecular Measurement. Thesis. Cardiff University. Website [online]. 2016 [retrieved on Aug. 8, 2018] URL:http://pdfs.semanticscholar.org/8266/276c3c14d24651cdf75dd4eddce262087451.pdf.

International Search Report and Written Opinion, dated Sep. 18, 2018, in corresponding PCT/US2018/33279, filed May 17, 2018, pp. 1-5.

Rago et al., Serial Assessment of Human Tumor Burdens in Mice by the Analysis of Circulating DNA, Cancer Research, Oct. 1, 2007, pp. 9364-9370, vol. 67, No. 19.

Sah, S et al, "Functional DNA quantification guides accurate next-generation sequencing mutation detection in formalin-fixed, paraffin-embedded tumor biopsies", Genome Medicine, Aug. 30, 2013, DOI: 10.1186/gm481 Refer to the ISR for relevant pgs/columns/para, vol. 5, No. 8.

International Searching Authority, International Preliminary Report on Patentability for International Patent Application No. PCT/US2018/033279 (dated Nov. 19, 2019).

International Searching Authority, International Search Report for International Patent Application No. PCT/US2018/033279 (dated Nov. 22, 2018).

International Searching Authority, Written Opinion of the International Searching Authority for International Patent Application No. PCT/US2018/033279 (dated Nov. 22, 2018).

* cited by examiner

SYSTEM AND METHOD FOR ISOLATION AND QUALIFICATION OF NUCLEIC ACIDS

CROSS-REFERENCE TO RELATED APPLICATIONS

This patent application is a continuation of the International Application Ser. No. PCT/US2018/033279 filed on May 17, 2018 which claims priority to and the benefit of U.S. Provisional Application No. 62/507,501, filed May 17, 2017 which is incorporated herein by reference as if set forth in its entirety.

STATEMENT REGARDING FEDERALLY SPONSORED RESEARCH

Not applicable.

SEQUENCE LISTING

The instant application contains a Sequence Listing which has been submitted electronically in ASCII format and is hereby incorporated by reference in its entirety. Said ASCII copy, created on Jun. 29, 2018, is named _P34273-WO_SL.txt and is 1,446 bytes in size.

BACKGROUND

The disclosure relates, in general, to sample preparation for next generation sequencing of nucleic acids and, more particularly, to a system and method for the isolation and qualification of nucleic acids.

Genotyping of tumor tissues at diagnosis is useful to guide proper therapy selection. Most commonly, this genotyping of the tumor is performed using a slide or curl from a tissue biopsy that has been fixed in formalin and embedded in paraffin (i.e., formalin fixed paraffin embedded tissue, or FFPET). However, the process of fixation and embedding, as well as storage of these FFPET samples (potentially for decades) generally leads to chemical damage of the DNA. This damage makes correct identification of tumor-specific variants more difficult, both by increasing the "noise" due to errors created by damaged DNA, as well as decreasing the "signal" by rendering processing of the FFPET-derived DNA with standard molecular biology techniques less efficient than the processing of other types of DNA using the same or similar techniques. In addition, isolation of DNA from FFPET samples is typically a time-consuming process that uses reagents such as xylene which can require additional safety precautions. Moreover, the isolation process can result in highly variable quantities of DNA that are of variable quality.

Accordingly, there is a need for new approaches that enable the efficient isolation of higher quality and greater quantities of DNA than other methods, thereby allowing for more confident variant detection at a lower limit of detection.

SUMMARY

The present invention overcomes the aforementioned drawbacks by providing a system and method for the isolation and qualification of nucleic acids.

In accordance with one embodiment of the present disclosure, a method includes isolating DNA from a source, thereby providing a composition comprising the isolated DNA, the isolated DNA having at least a first target region having a first length in nucleotides and a second target region having a second length in nucleotides, the second length being greater than the first length. The method further includes quantifying a total mass of the isolated DNA in the composition, quantifying a first quantification cycle ($C_q$) of the first target region and a second $C_q$ of the second target region in the composition, calculating a Q-ratio for the isolated DNA by dividing the second $C_q$ by the first $C_q$, determining a value for a quality-mass constant ($k_{Qm}$), estimating a required input mass for the isolated DNA by dividing the quality-mass constant ($k_{Qm}$) by the Q-ratio, and preparing the isolated DNA for sequencing if the total mass of the isolated DNA in the composition is equal or greater than the required input mass.

In one aspect, the length of the second target region is about 2 to about 10 times greater than the length of the first target region.

In another aspect, the length of the first target region is about 25 nucleotides to about 75 nucleotides and the length of the second target region is about 100 nucleotides to about 500 nucleotides.

In another aspect, the Q-ratio is indicative of the quality of the isolated DNA.

In another aspect, $k_{Qm}$ is about 10, and the Q-ratio is greater than 0.02.

In another aspect, the total mass of the isolated DNA in the composition is determined by spectroscopy.

In another aspect, the first $C_q$ of the first target region and the second $C_q$ of the second target region in the composition are determined by quantitative polymerase chain reaction (qPCR).

In another aspect, the source of the isolated DNA is formalin-fixed paraffin-embedded tissue (FFPET).

In another aspect, the isolated DNA is human genomic DNA.

In another aspect, at least one of the first target region and the second target region coincide with a long interspersed nuclear element (LINE).

In another aspect, the quality-mass constant ($k_{Qm}$) is determined by sequencing a plurality of regions of a plurality of isolated DNA samples. Each of the isolated DNA samples having a known input mass and a known Q-ratio. The quality-mass constant ($k_{Qm}$) is further determined by comparing a fraction ($F_D$) of the plurality of the regions with a selected depth of coverage as determined by the step of sequencing with a product of the input mass and the Q-ratio for each of the isolated DNA samples, identifying a minimum value for the product of the input mass and the Q-ratio at which FD is greater than a target FD, and setting the quality-mass constant ($k_{Qm}$) equal to the minimum value for the product of the input mass and the Q-ratio determined in the step of identifying.

In another aspect, $k_{Qm}$ is selected for a target FD of at least 0.95.

In another aspect, $k_{Qm}$ is 10, and the Q-ration is at least 0.02.

In another aspect, the present disclosure provides a kit for carrying out the disclosed method.

In another aspect, the kit includes a first pair of primers for amplifying the first target region, and a second pair of primers for amplifying the second target region.

In another aspect, the method includes combining the isolated DNA composition with a uracil N-glycosylase (UNG) in a first buffer to provide a first mixture. A portion of the isolated DNA composition including at least one uracil moiety. The method further includes incubating the first mixture under conditions suitable to degrade the portion of the isolated DNA composition, combining the first mixture with a dsDNA fragmentation enzyme to provide a second mixture, and incubating the second mixture under conditions suitable to fragment the isolated DNA composition. The step of degrading the portion of the isolated DNA composition with the UNG and the step of fragmenting the isolated DNA composition occur in the first buffer.

In accordance with another embodiment of the present disclosure, a method for calculating a quality-mass constant ($k_{Qm}$), includes sequencing a plurality of regions of a plurality of isolated DNA samples, each of the isolated DNA samples having a known input mass and a known Q-ratio, comparing a fraction (FD) of the plurality of the regions with a selected depth of coverage as determined by sequencing in step (i) with a product of the input mass and the Q-ratio for each of the isolated DNA samples, and identifying a minimum value for the product of the input mass and the Q-ratio at which FD is greater than a target FD.

In one aspect, the present disclosure provides a kit for carrying out the method of calculating a quality-mass constant ($k_{Qm}$).

In another aspect, the kit includes a first pair of primers for amplifying a first target region, and a second pair of primers for amplifying a second target region.

In another aspect, at least one of the first target region and the second target region coincide with a long interspersed nuclear element (LINE).

In accordance with another embodiment of the present disclosure, a method for preparing a composition comprising isolated DNA for sequencing includes combining an isolated DNA composition with a uracil N-glycosylase (UNG) in a first buffer to provide a first mixture. A portion of the isolated DNA composition including at least one uracil moiety. The method further includes incubating the first mixture under conditions suitable to degrade the portion of the isolated DNA composition, combining the first mixture with a double stranded DNA fragmentation enzyme to provide a second mixture, and incubating the second mixture under conditions suitable to fragment the isolated DNA composition. The step of degrading the portion of the isolated DNA composition with the UNG and the step of fragmenting the isolated DNA composition occur in the first buffer.

In one aspect, the isolated DNA composition is derived from formalin-fixed paraffin-embedded tissue (FFPET).

In another aspect, a kit is provided for performing the disclosed method.

In another aspect, the kit includes the first buffer, the UNG, and the double stranded DNA fragmentation enzyme.

In accordance with another embodiment of the present disclosure, a method includes isolating DNA from a source, thereby providing a composition including the isolated DNA. The isolated DNA has at least a first target region having a first length in nucleotides and a second target region having a second length in nucleotides. The second length is greater than the first length. The method further includes quantifying a total mass of the isolated DNA in the composition, quantifying a first concentration of the first target region and a second concentration of the second target region in the composition, calculating a Q-ratio for the isolated DNA by dividing the second concentration by the first concentration, determining a value for a quality-mass constant ($k_{Qm}$), estimating a required input mass for the isolated DNA by dividing the quality-mass constant ($k_{Qm}$) by the Q-ratio, and preparing the isolated DNA for sequencing if the total mass of the isolated DNA in the composition is equal or greater than the required input mass.

In one aspect, the length of the second target region is about 2 to about 10 times greater than the length of the first target region.

In another aspect, the length of the first target region is about 25 nucleotides to about 75 nucleotides and the length of the second target region is about 100 nucleotides to about 500 nucleotides.

In another aspect, the Q-ratio is indicative of the quality of the isolated DNA.

In another aspect, $k_{Qm}$ is about 10, and wherein the Q-ratio is greater than 0.02.

In another aspect, the total mass of the isolated DNA in the composition is determined by spectroscopy.

In another aspect, the first concentration of the first target region and the second concentration of the second target region in the composition are determined by quantitative polymerase chain reaction (qPCR).

In another aspect, the source of the isolated DNA is formalin-fixed paraffin-embedded tissue (FFPET).

In another aspect, the isolated DNA is human genomic DNA.

In another aspect, at least one of the first target region and the second target region coincide with a long interspersed nuclear element (LINE).

In another aspect, the quality-mass constant ($k_{Qm}$) is determined by sequencing a plurality of regions of a plurality of isolated DNA samples. Each of the isolated DNA samples has a known input mass and a known Q-ratio. The constant is further determined by comparing a fraction ($F_D$) of the plurality of the regions with a selected depth of coverage as determined in the step of sequencing with a product of the input mass and the Q-ratio for each of the isolated DNA samples, identifying a minimum value for the product of the input mass and the Q-ratio at which $F_D$ is greater than a target $F_D$, and setting the quality-mass constant ($k_{Qm}$) equal to the minimum value for the product of the input mass and the Q-ratio determined in the step of identifying.

In another aspect, $k_{Qm}$ is selected for a target $F_D$ of at least 0.95.

In another aspect, $k_{Qm}$ is 10, and the Q-ration is at least 0.02.

In another aspect, a kit is provided for carrying out the disclosed method.

In another aspect, the kit includes a first pair of primers for amplifying the first target region, and a second pair of primers for amplifying the second target region.

In another aspect, the method further includes combining the isolated DNA composition with a uracil N-glycosylase (UNG) in a first buffer to provide a first mixture. A portion of the isolated DNA composition includes at least one uracil moiety. The method further includes incubating the first mixture under conditions suitable to degrade the portion of the isolated DNA composition, combining the first mixture with a dsDNA fragmentation enzyme to provide a second mixture, and incubating the second mixture under conditions suitable to fragment the isolated DNA composition. The step of degrading the portion of the isolated DNA composition with the UNG and the step of fragmenting the isolated DNA composition occur in the first buffer.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

I. Definitions

Figure 1:
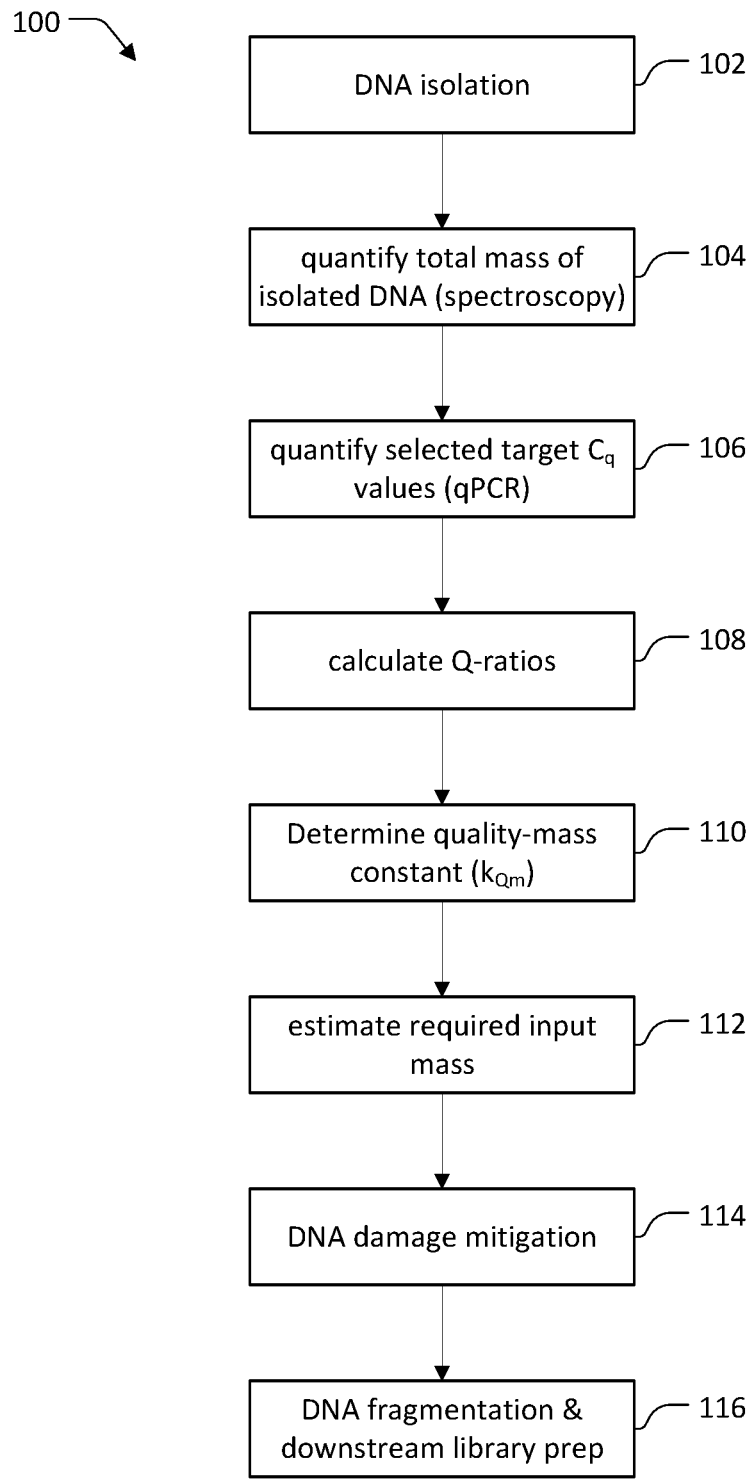
FIG. 1 is a schematic flow diagram depicting an embodiment of a method for the isolation and qualification of DNA according to the present disclosure.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Approximately: As used herein, the term "approximately" or "about", as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level, and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biological Sample: As used herein, the term "biological sample" typically refers to a sample obtained or derived from a biological source (e.g., a tissue or organism or cell culture) of interest, as described herein. In some embodiments, a source of interest comprises or consists of an organism, such as an animal or human. In some embodiments, a biological sample is comprises or consists of biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample is comprises or consists of cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Comprising: A composition or method described herein as "comprising" one or more named elements or steps is open-ended, meaning that the named elements or steps are essential, but other elements or steps may be added within the scope of the composition or method. It is to be understood that composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and dosed-ended composition or method "consisting of" (or "consists of") the named elements or steps to the exclusion of any other unnamed element or step. In any composition or method disclosed herein, known or disclosed equivalents of any named essential element or step may be substituted for that element or step.

Designed: As used herein, the term "designed" refers to an agent (i) whose structure is or was selected by the hand of man; (ii) that is produced by a process requiring the hand of man; and/or (iii) that is distinct from natural substances and other known agents.

Determine: Those of ordinary skill in the art, reading the present specification, will appreciate that "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgap-dna.CMP matrix.

Quantification cycle ($C_q$): As used herein, the term "Quantification cycle" or "$C_q$" refers to the cycle at which fluorescence from amplification exceeds the background fluorescence in a quantitative PCR (qPCR) assay. The term $C_q$ is alternatively referred to as the threshold cycle ($C_t$), crossing point ($C_p$), and take-off point (TOF); however, each of the terms are equivalent and are therefore used interchangeably. Notably, a lower $C_q$ correlates with higher target expression in a sample.

Sample: As used herein, the term "sample" refers to a substance that is or contains a composition of interest for qualitative and or quantitative assessment. In some embodiments, a sample is a biological sample (i.e., comes from a living thing (e.g., cell or organism). In some embodiments, a sample is from a geological, aquatic, astronomical, or agricultural source. In some embodiments, a source of interest comprises or consists of an organism, such as an animal or human. In some embodiments, a sample for forensic analysis is or comprises biological tissue, biological fluid, organic or non-organic matter such as, e.g., clothing, dirt, plastic, water. In some embodiments, an agricultural sample, comprises or consists of organic matter such as leaves, petals, bark, wood, seeds, plants, fruit, etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Synthetic: As used herein, the word "synthetic" means produced by the hand of man, and therefore in a form that does not exist in nature, either because it has a structure that does not exist in nature, or because it is either associated with one or more other components, with which it is not associated in nature, or not associated with one or more other components with which it is associated in nature.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, a variant may also have one or more functional defects and/or may otherwise be considered a "mutant". In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

Whitelist: As used herein, a "whitelist" is a focused list of mutations of exceptional biological or clinical significance. For example, a whitelist can include a set of known single nucleotide variants (SNVs) that are implicated in oncology.

II. Detailed Description of Certain Embodiments

As also discussed above, in various situations it may be useful to provide methods for the isolation and qualification of nucleic acids derived from various biological samples or other like sources. For example, various cancer diagnostics rely upon the isolation of DNA from a tissue biopsy that has been fixed in formalin and embedded in paraffin (i.e., FFPET). However, DNA isolated from FFPET samples is often degraded or otherwise damaged rendering correct identification of tumor-specific variants more difficult. Accordingly, standard molecular biology techniques useful for isolating DNA from other sources (e.g., fresh tissue), may be less efficient for the recovery of DNA from FFPET. Moreover, current approaches for isolating nucleic acids from FFPET can have inconsistent results, resulting in DNA of both variable quantity and quality.

These and other challenges may be overcome with a system and method for the isolation and qualification of nucleic acids according to the present disclosure. In order to account for difficulties in DNA isolation from FFPET samples, the present disclosure provides for methods that enable efficient isolation of nucleic acids with higher quality and quantity than other commercially available approaches. In one aspect of the disclosed method, a qPCR-based assay for DNA quality determination ensures that a sufficient amount of DNA is provided as an input to library preparation for next generation sequencing, thereby enabling accurate variant detection. In another aspect, an optimized molecular biology approach reduces error rates and maximizes efficiency to allow for improved signal-to-noise, allowing more confident variant calling at a lower limit of detection.

Notably, the present disclosure is, at least in part, based on the surprising discovery that there is a correlation between depth of coverage as determined by next generation sequencing for a given DNA sample and the product of (i) the input mass ($m_i$) of the DNA, and (ii) the Q-ratio, which describes the quality of the DNA. This correlation is leveraged as part of the disclosed methods to define a quality-mass constant ($k_{Qm}$), which can be used to predict the minimum required input mass for newly isolated DNA samples ahead of sequencing. For example, following isolation of DNA from an FFPET sample, the isolated DNA is subjected to two assays. In a first assay, the total mass of the isolated DNA is measured. In a second assay, the $C_q$ values (and additionally, or alternatively, the concentrations) of two differently sized target regions within the isolated DNA are determined, with either an equation relating the $C_q$ values or the ratio of the two concentrations providing a quality score or "Q-ratio". By dividing the quality-mass constant ($k_{Qm}$) by the Q-ratio, an indication of the required mass of DNA for sequencing can be determined for that specific sample. In the case that the total mass of the isolated DNA is less than the required mass of DNA as estimated using $k_{Qm}$ and the Q-ratio, then the determination can be made to forego sequencing, knowing that there may not be enough material to generate useful sequencing data.

It will be appreciated that, in addition to the identification and implementation of $k_{Qm}$ for characterizing nucleic acids, the present disclosure more generally provides for a method for isolation of DNA, estimation of the quality of the isolated DNA, calculation of the required input mass of DNA for library preparation for next generation sequencing, and pretreatment of the DNA for input into downstream library preparation protocols.

In one embodiment, the present disclosure includes a method for the isolation of DNA from FFPET. Isolation of the DNA can be achieved using an optimized version of the KAPA Express Extract kit (ROCHE). Following isolation, the quality of the DNA is measured using both standard spectroscopy as well as a quantitative PCR (qPCR) assay targeting two or more specific target sequences or regions. In one aspect, spectroscopy techniques such as absorbance or fluorescence are used to measure the mass or concentration of DNA in the sample. Commercial instruments available for such measurements include the NanoDrop spectrophotometer (THERMO FISHER) and QUBIT fluorometer (THERMO FISHER). In another aspect, a qPCR-based method targeting the amplification of differently sized sequences (e.g., KAPA Human Genomic DNA Quantification and QC Kit (ROCHE)) can be used to measure either or both of the $C_q$ values and the concentrations of those sequences as well as the quality of the isolated DNA through the use of a Q-ratio.

Another component of the disclosed method includes a calculation of the required input mass of DNA for library preparation for next generation sequencing. In particular, the surprising discovery has been made that the required input mass can be derived using an equation relating the proper input mass of DNA into library prep to the measured quality of the DNA (Q-ratio) and a quality-mass constant ($k_{Qm}$). In yet another aspect, the disclosed method includes a library preparation pretreatment encompassing a combined polishing and fragmentation protocol that quickly and efficiently reduces errors due to deamination of cytosines, and fragments the DNA into the proper size for input into library preparation. In one aspect, the workflow is designed such that the resulting pretreated DNA is compatible with downstream library preparation workflow, thereby eliminating the need for additional clean-up steps.

Figure 2:
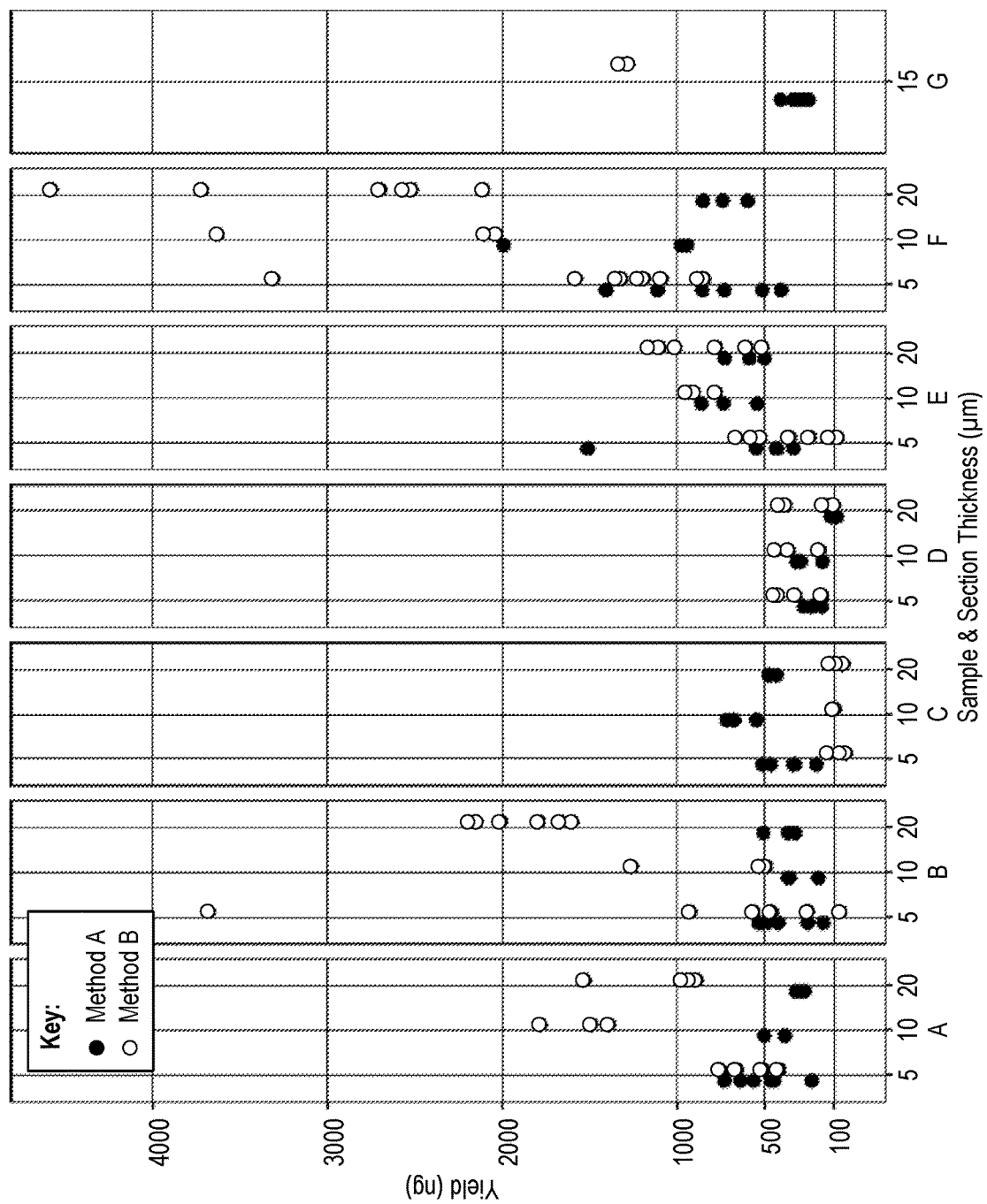
FIG. 2 is a scatter plot showing the yield of DNA in nanograms from 5-20 μm thick curls obtained from a set of seven unique FFPET samples. For samples A-F, curls were obtained with a thickness of 5, 10, or 20 μm, whereas curls were obtained from sample G with a thickness of 15 μm only. For each sample, DNA was isolated using either an existing commercial DNA isolation kit (method A) or the DNA isolation method of the present disclosure (method B). Each data point on the plot represents data for a single curl from the corresponding sample.
Figure 3:
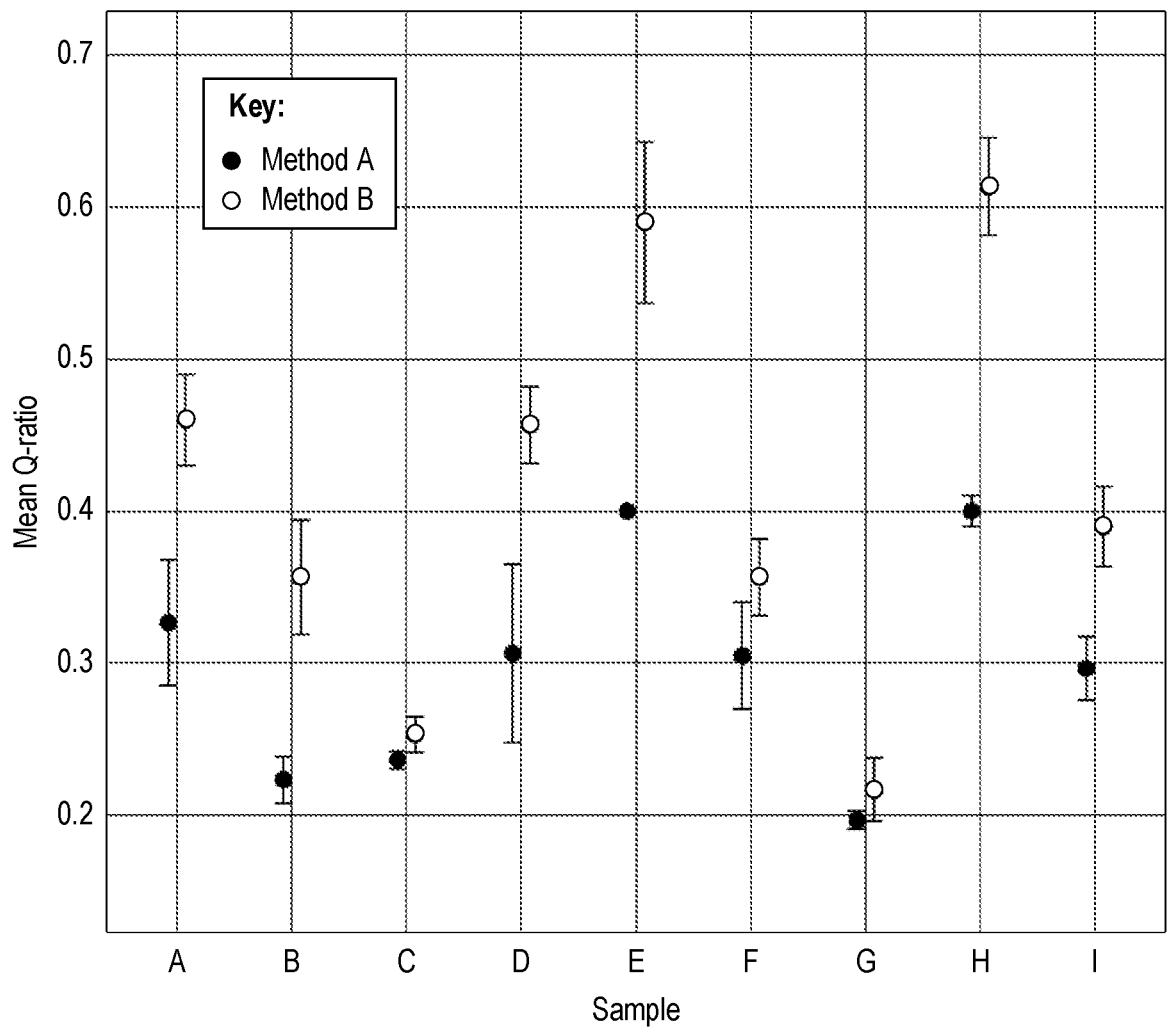
FIG. 3 is a scatter plot showing the mean Q-ratio calculated for DNA isolated from 10 μm thick curls obtained from a set of nine unique FFPET samples (samples A-I). For each sample, DNA was isolated using either an existing commercial DNA isolation kit (method A) or the DNA isolation method of the present disclosure (method B). Q-ratios were calculated based on the quantification cycle ($C_q$) values for two differently sized amplicons as estimated by qPCR (see text for details). Error bars for each data point are indicative of the standard deviation (N=3).

Turning now to FIG. 1, a method 100 according to the present disclosure includes a step 102 of nucleic acid isolation. In the step 102, nucleic acids can be isolated from a number of different sources or samples. In one embodiment, the nucleic acids are DNA isolated from FFPET; however, it will be appreciated that the isolation of RNA from FFPET or another source is also within the scope of the present disclosure. In the case of FFPET, one example DNA isolation method includes the protocol and reagents associated with the KAPA Express Extract Kit (ROCHE). In another embodiment, the DNA is isolated from FFPET using an improved version of the protocol distributed with the KAPA Express Extract Kit (ROCHE) described herein. In particular, the present disclosure provides for a number of newly discovered improvements that may be made to the aforementioned protocol (see Example 3). In general, water, buffer, and enzyme are added to an FFPET curl or slide. The mixture is incubated at 75° C. for 1 hour with shaking or occasional vortexing, and then cleaned up. While the protocol includes a step of centrifuging the sample to separate a wax layer from a liquid layer, this step may be omitted. In one aspect, omitting this step may reduce hands on time, improve the ease of automating the protocol, reduce turn-around time, or a combination thereof. For example, removing the need for a centrifuge enables the protocol to be performed using only a liquid handling robot without the need for additional equipment. Notably, the yield of DNA isolated from FFPET using the improved method disclosed herein was found to be comparable to or better than the commercially available DNA isolation kits (FIG. 2). Similarly, the quality of the isolated DNA as measured through the use of a Q-ratio was found to be comparable to or better than the commercially available DNA isolation kits (FIG. 3).

With continued reference to FIG. 1, a next step 104 of the method 100 includes quantifying the DNA concentration using a spectroscopic approach such as absorbance or fluorescence measurements. Quantification of DNA concentrations using spectroscopic methods is well known in the art and can be achieved using a variety of commercially available instruments and reagents that are especially designed for the purpose. Example commercial instruments available for such measurements include the NanoDrop spectrophotometer (THERMO FISHER) and QUBIT fluorometer (THERMO FISHER). In general, a solution phase sample of the isolated DNA is measured using a spectrophotometer to determine the concentration of DNA present in the solution. In one aspect, the spectrophotometer is used to determine the concentration of single stranded DNA (ssDNA), double stranded DNA (dsDNA), or a combination thereof.

The method 100 further includes estimating the quality of the DNA by first quantifying selected target $C_q$ values via qPCR in a step 106 and then calculating a quality ratio (Q-ratio) in a step 108. In the step 106, primers are designed to amplify specific sequences or regions that should be present in the isolated DNA. By amplifying regions of different sizes (i.e., sequences having different lengths in nucleotides), an estimate of the extent of degradation of the DNA—and therefore of the quality of the DNA—can be determined. This approach is based on the theory that as a sample becomes increasingly degraded due to DNA damage or the like, fewer copies of the full length sequence targeted by the primers in qPCR experiment will exist, and therefore will be less likely to result in successful amplification. Moreover, DNA damage will have a greater effect on the ability to amplify a particular sequence (target region) as the length of the sequence in nucleotides increases. By leveraging this phenomenon, an estimate of the quality of the DNA can be determined by first measuring the $C_q$ values (and optionally the concentrations) of differently sized target regions via qPCR in the step 106, and then taking a ratio of the $C_q$ value of first (longer) target region to the $C_q$ value of a second (shorter) target region in the step 108. The resulting Q-ratio will have a value of ~1.0 for a DNA sample with little to no degradation, whereas the Q-ratio will have a value less than 1.0 for a DNA sample exhibiting at least some degradation.

One approach for estimating a Q-ratio is described in the KAPA Human Genomic DNA (hgDNA) Quantification and QC Kit (ROCHE). In this approach, primers are used to amplify 41 bp, 129 bp, and 305 bp target regions present in an hgDNA sample. The resulting $C_q$ values of the hgDNA samples for the 41 bp, 129 bp, and 305 bp assays are used to calculate a Q-ratio for the $C_q$ values determined via the 41 bp assay relative to $C_q$ values determined via either of the 129 bp assay and the 305 bp assay (see Example 1).

A second approach for estimating a Q-ratio replaces the 41 bp, 129 bp, and 305 bp assays described in the KAPA Human Genomic DNA Quantification and QC Kit (ROCHE) with assays targeting long interspersed nuclear elements (LINEs). In general, this approach takes advantage of two primer sets targeting regions coinciding with the LINEs of the human genome, one of which is 66 nucleotides in length, and one of which is 191 nucleotides in length. Because these regions target the LINE (which is copied thousands or millions of times in the human genome), orders of magnitude less DNA can be used as input. In one embodiment, to maximize ease of use, an FFPET-derived DNA sample or control genomic DNA sample is diluted 500-fold, then used as input for this assay. In another embodiment, the sample or the control genomic DNA sample is diluted by a different amount or not diluted at all. Using this assay on the FFPET-derived DNA samples, as well as on control genomic DNA, a score for the quality of the DNA samples (ranging from 0 to 1) can be determined (see Example 2). In yet another aspect, the Q-ratio can be normalized to a Q-ratio calculated for a genomic standard (see Example 3).

Figure 4:
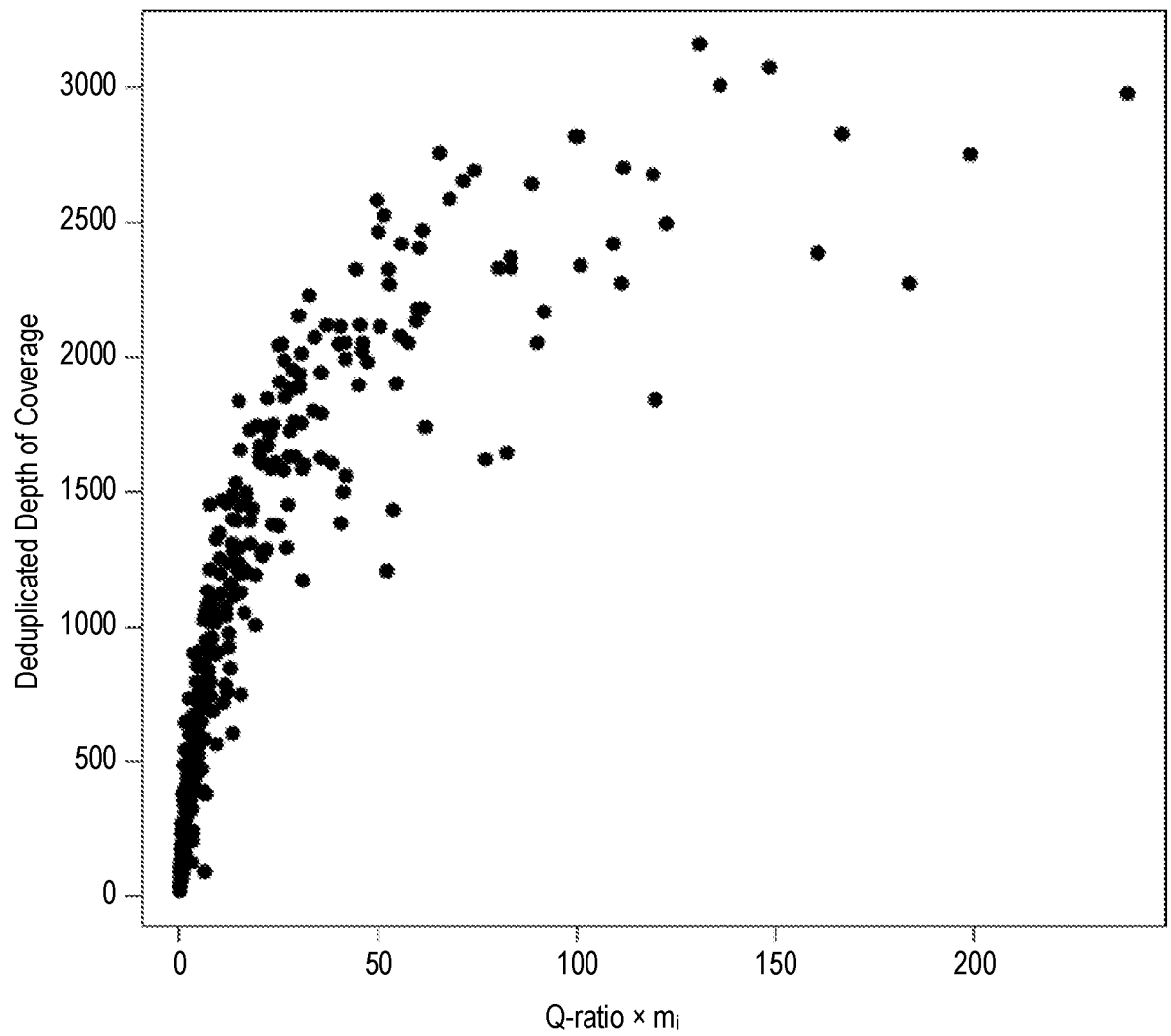
FIG. 4 is a scatter plot showing the relationship between deduplicated depth of coverage as determined by next generation sequencing and the product of the input mass and the Q-ratio calculated for DNA isolated from different FFPET samples. Q-ratios were calculated using the disclosed LINE element approach (see text for details). Each data point on the plot represents data for a single sample. The deduplicated depth of coverage exhibited a positive correlation with Q-ratio with a Pearson correlation coefficient (R) of 0.794.

Continuing with FIG. 1, in a step 110 of the method 100, a quality-mass constant defined as $k_{Qm}$ is determined. In one aspect, the surprising discovery was made that there is a strong correlation between the product of the experimental input mass (as determined by spectrophotometer) and the Q-ratio (as determined by qPCR) with the deduped sequencing depth determined empirically from sequencing (FIG. 4). In particular, for at least the data set depicted in FIG. 4, the deduplicated depth of coverage exhibited a positive correlation with Q-ratio with a Pearson correlation coefficient (R) of 0.794. Given this correlation, a threshold $k_{Qm}$ can be identified based on a desired sequencing outcome (e.g., minimum deduped sequencing depth). By fixing the value of $k_{Qm}$, the surprising discovery has been made that the required input mass for NGS library prep can be predicted in a step 112 of the method 100 by dividing $k_{Qm}$ by the Q-ratio calculated for a given sample.

Figure 5:
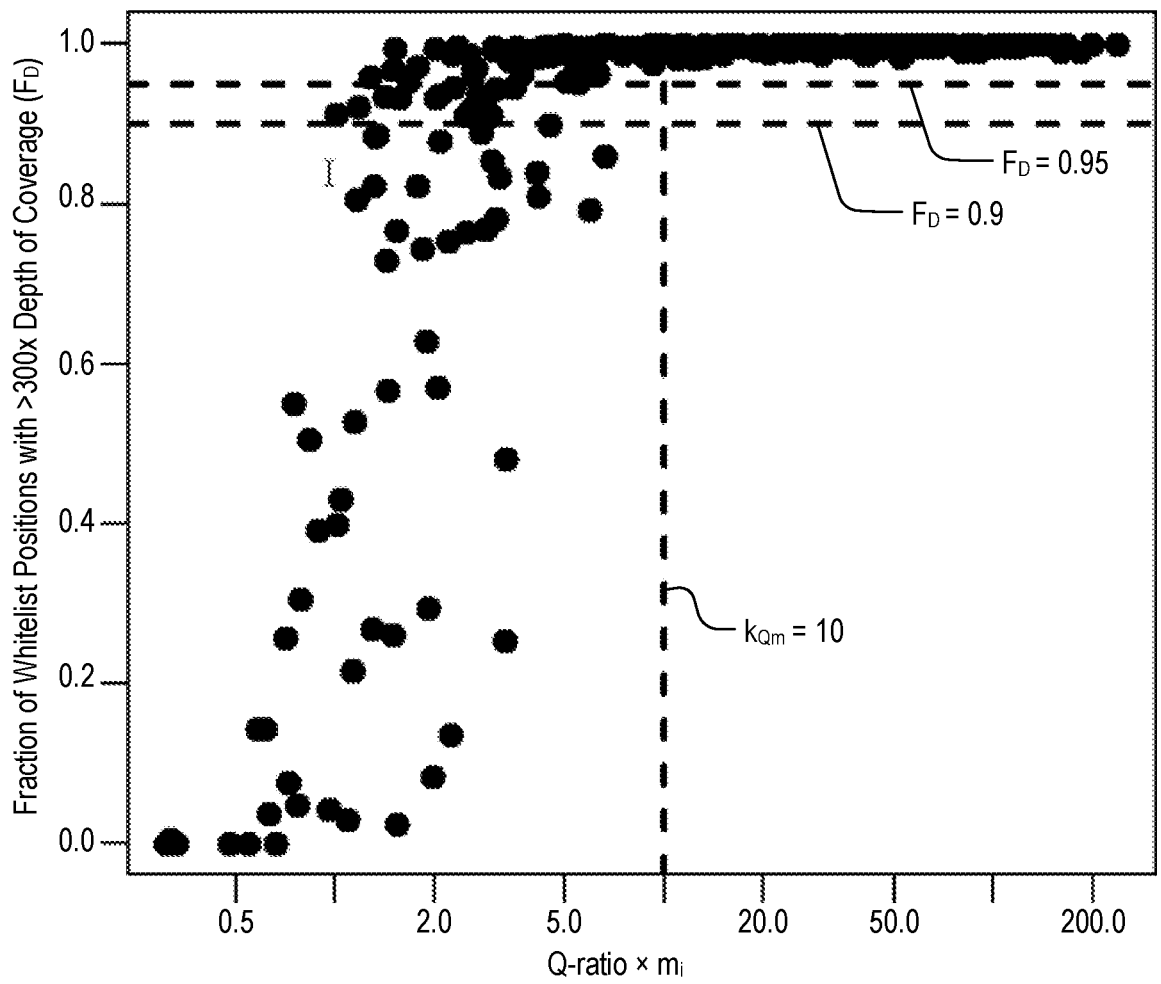
FIG. 5 is a scatter plot showing the fraction of whitelist positions with greater than 300× depth of coverage ($F_D$) as a function of the product of the input mass and the Q-ratio calculated for DNA isolated from different FFPET samples. Q-ratios were calculated using the disclosed LINE element approach (see text for details). Each data point on the plot represents data for a single sample. The dashed lines indicate that for a quality-mass constant ($k_{Qm}$)≥10, at least 95% of the whitelist positions exhibited greater than 300× depth of coverage for nearly all samples with a Q-ratio>0.02.

In the step 112, the required input mass ($m_i$) for a given NGS experiment is determined by dividing $k_{Qm}$ (determined in the step 110) by the Q-ratio calculated for a given sample (calculated in the step 108). In one embodiment of the present disclosure, the value of $k_{Qm}$ is selected to maximize the percent of samples with an input mass resulting in greater than 95% of positions with enough depth for variant calling down to 5%. Empirical data suggests that greater than 300× sequencing depth is necessary to call allele frequency down to 5% using the disclosed methods. As shown in FIG. 5, for $k_{Qm}=10$, the input mass as determined by dividing $k_{Qm}$ by the Q-ratio gives greater than 300× depth for at least 95% of whitelist positions for nearly all samples having a Q-ratio greater than 0.02. Other allele frequency cutoffs could lead to other equations. For example, it was observed that for $k_{Qm}=20$, the input mass derived from the equation 20/(Q-ratio) gives greater than 500× depth for at least 95% of positions for nearly all samples with a Q-ratio greater than 0.04. Notably, this approach can be used to determine which samples can be called with an allele frequency down to 3%.

In one aspect, $k_{Qm}$ may be affected by a number of factors such as the age or quality of a given sample, the protocol used to isolated the nucleic acids from the sample, the instrument used to sequence the isolated nucleic acids, and the like. However, the overall effect on $k_{Qm}$ can be relatively minimal. In particular, very consistent values for $k_{Qm}$ (for specified allele fraction) have resulted in spite of (for example) the use of a variety of FFPET samples of varying age and quality. That said, it will be appreciated that it can be useful to calculate (or recalculate) the value of $k_{Qm}$ for a given DNA isolation protocol, library preparation methodology, sequencing methodology, or a combination thereof.

Following calculation of the required input mass in the step 112, a step 114 of the method 100 includes mitigation of DNA damage. Since deamination of cytosine is a common type of damage in FFPET samples, enzymes that remove deaminated cytosine (i.e., uracil) can be used to reduce the error rate when using sequencing assays on FFPET samples. Accordingly, the present disclosure provides for methods of treating isolated DNA with a uracil-DNA glycosylase (UNG) to provide higher quality DNA for sequencing.

The method 100 further includes a step 116 of DNA fragmentation and, optionally, downstream library preparation. In order to work with library preparation protocols for sequencing that rely on ligation of adapter sequences, FFPET samples must be fragmented. To maximize ease of use, the present disclosure provides for methods that use the same buffer for at least the step 114 (including treatment with UNG) and the step 116 (including enzymatic fragmentation) of the method 100.

In one embodiment of the present disclosure, the target regions used to calculate a Q-ratio can coincide with the human long interspersed nuclear element (LINE) sequence. Various pairs of amplification primers can be used for generating LINE amplicons. As shown in Table 1, one example set of primer pairs includes a first primer pair for amplification of a 66 bp fragment, a second primer pair for amplification of a 191 bp fragment, and a third primer pair for amplification of a 330 bp fragment.

TABLE 1

| Target Region | Primer Sequence | | Tm (° C.) |
|---|---|---|---|
| LINE 66bp | F: TTGCGGAAGTCAGTGTGG | (SEQ ID NO: 1) | 59.90 |
| | R: GATGGCTGGGTCAAATGGTA | (SEQ ID NO: 2) | 60.40 |
| LINE 191bp | F: ACTTGGAACCAACCCAAATG | (SEQ ID NO: 3) | 58.35 |
| | R: TGAGAATATGCGGTGTTTGG | (SEQ ID NO: 4) | 58.35 |
| LINE 330bp | F: CAAACAACCCCATCAAAAAGTG | (SEQ ID NO: 5) | 58.95 |
| | R: GATGGCTGGGTCAAATGGTA | (SEQ ID NO: 2) | 60.40 |

The use of LINE sequences as target regions for qPCR overcomes the limitations of other single or multiple copy designs because the sensitivity is highly increased and thus less material for the analysis is required. Choosing LINE sequences as a target is of particular advantage, because LINE sequences are more or less randomly distributed all over the human genome. A respective LINE assay to investigate the degree of DNA damage therefore reflects the quality status of the respective sample all over the complete genome, whereas an analysis of one or more single copy genes only represents the DNA quality of the sample with respect to particular genomic loci. Similarly, analysis of other multi copy genes not randomly distributed all over the genome also does not indicate the quality of the sample as a whole.

For the determination of the quality of a sample such as a FFPET sample, the $C_q$ values measured with different amplicon lengths can be used to calculate a Q-ratio. Notably, methods for determining a Q-ratio for a DNA sample can be carried out in different modes. In one mode, the relative abundance of a first shorter amplicon and a second longer amplicon generated from the same amount of sample DNA is determined directly by determining a $C_q$ value for each amplicon and comparing those values. In another mode, the $C_q$ values are first normalized against $C_q$ values obtained for a standard DNA sample, which is amplified in parallel within the same experiment. In a further mode, the $C_q$ values are normalized against a standard curve generated from known amounts of target DNA. In yet another mode, $C_q$ values, in conjunction with one or more DNA standards, are used to first calculate a concentration for each amplicon, with the ratio or the concentrations used to determine a Q-ratio.

To obtain a sample specific quality ratio without measuring any standard, it is only necessary to measure the $C_q$ values for two LINE amplicons of different length at the same sample concentration and determine the differences of the $C_q$ values. The difference is a measure for the relative abundance of the two amplicons (a first, shorter amplicon, and a second, longer amplicon) in this sample. The abundance is calculated according to Equation 1, where Q-ratio is an indicator of the relative quality and $C_{q1}$ and $C_{q2}$ are the mean $C_q$ values from the qPCR for the first, shorter amplicon and the second, longer amplicon, respectively.

$$Q\text{ ratio} = 2^{(average(C_{q1}) - average(C_{q2}))} \quad \text{(Eq. 1)}$$

If $C_{q1}$ and $C_{q2}$ are identical or almost identical, then the Q-ratio=1 or close to 1 and the sample is a high quality sample. However, if the sample is more degraded, than the Q-ratio will be less than 1. If standard curves are available for a sample with known good quality (e.g., genomic DNA from blood cells) the Q-ratio can be calculated as the ratio of the concentrations obtained for an unknown sample from these standard curves. Therefore at least two standard curves for two different amplicon lengths, along with the values of the unknown sample for the same two amplicons, are necessary. The Q-ratio is then calculated according to Equation 2 as the ratio of concentration of the second, longer amplicons ($[C_2]$) to the concentration of the first, shorter amplicon ($[C_1]$).

$$Q\text{ ratio} = \frac{[C_2]}{[C_1]} \quad \text{(Eq. 2)}$$

The determination of the Q-ratio could also be performed by using a reference sample. As the absolute difference of concentrations between the unknown and the reference sample is mostly not known, the difference in the $C_q$ values has to be corrected for this. Therefore the $C_q$ values for a short amplicon from the sample and the reference sample are determined. The difference of the $C_q$ values of these amplicons may serve as a measure for the difference of the concentrations of the sample and the reference sample. In parallel, the $C_q$ values for a longer amplicon from the sample and the reference sample are determined. The difference of the $C_q$ values of these longer amplicons will serve as a measure for the difference in the DNA quality of the sample and the reference sample. One advantage of this method is that only one standard sample per measurement (e.g., microtiter plate) is needed.

In a further embodiment, the present disclosure provides specific reagents and kits for executing the inventive method. In a first aspect, the present invention provides a first primer pair of amplification primers according to SEQ ID NOs: 1 and 2. The present invention also provides a second pair of amplification primers according to SEQ ID NOs: 3 and 4. The present invention also provides a third pair of amplification primer according to SEQ ID NOs: 5 and 2. Two or three of these pairs of amplification primers may constitute a kit for executing the inventive method as disclosed above. Such a kit may further comprise a thermostable DNA polymerase, deoxynucleotides and other reagents necessary for performing a PCR amplification reaction. Moreover, kits may be provided with reagents supporting any of the methods disclosed herein.

It will be appreciated that the methods of the present disclosure are applicable to the isolation and qualification of nucleic acids isolated from a variety of samples. Whereas several examples are described for the isolation of genomic DNA from FFPET, further embodiments of the present disclosure relate to the isolation of nucleic acids from yet other sources. For example, the efficiency of certain cell-free DNA (cfDNA) assays could be predicted or improved by determining the abundance of cfDNA relative to the abundance of high molecular weight DNA in a particular example. Accordingly, aspects of the present disclosure are applicable to the isolation and qualification of cfDNA from blood or plasma. With respect to cfDNA, a Q-ratio can be derived as described herein; however, in this case, a low Q-ratio is indicative of a higher abundance of smaller fragments corresponding to cfDNA. That is, as cfDNA is generally ~170 nucleotides in length, $C_q$ values for amplicons targeting smaller fragments (i.e., <170 nt) can be compared with $C_q$ values for amplicons targeting larger fragments (i.e., >170 nt) to determine the relative abundance of cfDNA in the sample.

EXAMPLES

The following Examples are meant to be illustrative and are not intended to be limiting in any way.

Example 1

The present example describes a method for calculating Q-ratios for DNA isolated from any source using the KAPA Human Genomic DNA (hgDNA) Quantification and QC Kit (ROCHE). Initially, a set of DNA Standards was prepared according to Table 2.

TABLE 2

| DNA Standard | Concentration (pg/μL hgDNA) |
| --- | --- |
| 1 | 2500 |
| 2 | 625 |
| 3 | 156 |
| 4 | 39.1 |
| 5 | 9.77 |

The DNA standards comprised a 4-fold dilution series of a 610 bp dsDNA template. Background-subtracted (normalized) amplification curves and the quantification cycle ($C_q$) scores for replicate data points obtained vis a standard qPCR experiment were reviewed, and obvious outliers were excluded. All samples that fell outside the range of the standard curve (i.e., that returned an average $C_q$ score lower than that of DNA standard 1, or higher than that of DNA standard 5) were excluded.

Software associated with the qPCR instrument was used to generate standard curves and to calculate the concentrations of the hgDNA samples for 41 bp, 129 bp, and 305 bp assays. Standard curves were used only if the R2≥0.99 and the calculated reaction efficiency was 90-110%.

The average concentration (from triplicate qPCR assays) was calculated for each hgDNA sample dilution taking into account any dilution performed during sample preparation, to calculate the concentration of each undiluted sample.

Q-ratios were calculated using one of two different approaches. In a first approach, the Q-value was calculated from the measured $C_q$ values according to Equation 1. In a second approach, Q-ratios were calculated according to Equation 2 by taking the ratio of the concentration calculated using an assay for a first target by the concentration calculated using an assay for a second target. For example, The Q305/Q41 ratio was obtained by dividing the concentration calculated using the 305 bp assay by the concentration calculated using the 41 bp assay.

Example 2

The present example describes a method for calculating Q-ratios for DNA isolated from any source using LINE elements.

All experiments were performed in a white LIGHTCYCLER 480 multiwell plate 384 on a LIGHTCYCLER instrument according to the manufacturer's instructions, using the FastStart Essential DNA Green Master kit (ROCHE ID No. 06924204001) for setting up the PCR amplification reaction.

A first primer pair according to SEQ ID NOs: 1 and 2 was used to amplify a 66 bp LINE amplicon, and a second primer pair according to SEQ ID NOs: 3 and 4 was used to amplify a 191 bp LINE amplicon. Optionally, a third primer pair according to SEQ ID NOs: 5 and 2 was used to amplify a 330 bp LINE amplicon. For amplification, a primer concentration of 0.4 µM each was used.

Five microliter of the diluted DNA sample was distributed to appropriate wells of a multiwell plate. After this the master mix was added. Experiments were always done in triplicates.

Thermocycling was performed in a 104 total volume as described in Table 3.

TABLE 3

| Temperature (° C.) | Time (sec) | Ramp (° C./s) | Cycles |
| --- | --- | --- | --- |
| 95 | 600 | 4.4 | 1 |
| 95 | 10 | 4.4 | 40 |
| 60 | 30 | 2.2 | |
| 72 | 30 | 4.4 | |

The data were analyzed using the standard analysis of the LIGHTCYCLER 96 SW 1.1 software and the results were exported into an Excel sheet where remaining calculations were done. The Q-ratio was calculated according to Equation 1.

Example 3

The present example describes a method for FFPET DNA isolation, qualification, and preparation for NGS. The method begins with DNA isolation from FFPET. For preparation of FFPET, FFPET curls were placed in 1.5 mL Eppendorf tubes. When using slides, as much tissue as possible was carefully scraped into 1.5 mL tubes with a razor blade. For preparation of the extraction master mix, the following mixture was prepared as described in Table 4.

TABLE 4

| Extraction Master mix | |
| --- | --- |
| Reagent | Volume per reaction |
| Nuclease-Free Water | 88 µL |
| 10X Express Extract Buffer | 10 µL |
| 1 U/µL Express Extract Enzyme | 2 µL |

The master mix in Table 4 was mixed by vortexing and centrifuged, followed by the addition of 100 µL of the master mix to each tube containing FFPET. The tubes were well mixed by vortexing and quickly spun to get the tissue as submersed in liquid as possible. Tubes were incubated in a thermomixer at 75° C. and 2000 RPM with the lid on for 1 hour. If a thermomixer was not available, tubes were incubated at 75° C. in a heat block for 1 hour. For the first 10 minutes, tubes were mixed by vortexing for 10 seconds every 2 minutes, and then mixed again by vortexing at the 30 minute mark.

Following the 1 hour incubation, tubes were centrifuged at 20,000×g for 5 minutes to pellet the remaining cellular debris and form a wax layer on top of the liquid. A pipette tip was poked through the wax layer (if present) and the liquid was transferred to strip tubes. As much liquid as possible was transferred while avoiding cellular debris/wax carryover. It was noted that wax carryover can leave the solution cloudy, even after bead clean-up. However, this was not observed to impact downstream applications.

In a next step of the method, extraction cleanup was achieved using KAPA Pure Beads (ROCHE) at a ratio of KAPA Pure Beads (ROCHE) to sample of 1.8:1.0. KAPA Pure Beads (ROCHE) were set out at least 15 minutes prior to use to bring them to room temperature. As the KAPA Pure Beads (ROCHE) are light sensitive, they were protected from light when not in use in order to avoid degradation of the buffer and loss of sample. Next, 180 µL of KAPA Pure beads were added to each sample and mixed well by pipetting or vortexing. Samples were incubated for 10 minutes at room temperature. The beads were then captured on a magnet for 2-3 minutes and the supernatant was discarded. With beads still on the magnet, the beads were washed with 200 µL of freshly prepared 80% ethanol. Samples were then incubated at room temperature for 30 seconds followed by removal of the supernatant. Wash and incubation with 80% ethanol was repeated for a 2nd wash. Tubes were then quickly centrifuged to bring the remaining liquid to the bottom, and the tubes were returned to the magnet in order to remove any remaining ethanol. Beads were air dried on the magnet for 3 minutes. Tubes were then removed from the magnet and the beads were resuspended in 40 µL of 10 mM Tris-HCl at pH 8 followed by incubation at room temperature for 2 minutes. Samples were then centrifuged and the beads were pelleted on a magnet. The eluate containing extracted DNA was transferred to fresh strip tubes. In the case that samples were not immediately subjected to downstream processing, the samples were stored at −20° C. for up to 1 month.

For quality control and testing of FFPET-extracted DNA, the concentration of individual samples was quantified with a QUBIT dsDNA HS Assay Kit (THERMO FISHER). Optionally, DNA was visualized by size distribution by diluting samples to 1-5 ng/µL and analyzing with a high sensitivity bioanalyzer. Quantitative PCR was used to determine input DNA quality based on the 191/66 bp Q-ratio. Each sample, standard, and no template control (NTC) was processed with at least three technical replicates. The input DNA and genomic standard were diluted 500-fold in water and to a minimum final volume of 24 µL plus excess. The genomic standard was included in each qPCR run. The following master mix for each primer premix was prepared separately (66 bp and 191 bp) as described in Table 5.

TABLE 5 qPCR Master Mix

| Reagent | Volume per reaction |
| --- | --- |
| ROCHE FastStart Essential DNA Green Master (2X) | 5 µl |
| Primer Premix (10X) | 1 µl |

The master mix in Table 5 was mixed by vortexing and centrifuged. Then, 6 µL of the appropriate master mix was added to each well to be used of a 384 well plate. To each of the applicable wells, 4 µL of the diluted sample, the genomic standard, and the NTC (water) were added. The well plate was then sealed and centrifuged briefly. Analysis by qPCR was performed according to the thermocycler profile shown in Table 6.

TABLE 6

Thermocyder profile

| Stage | Temp (° C.) | Duration | Ramp Rate (° C./sec) | Cycles |
| --- | --- | --- | --- | --- |
| Initial denaturation | 95° C. | 10 min | 4.4 | 1 |
| Denaturation | 95° C. | 10 sec | 4.4 | 40 |
| Annealing | 60° C. | 30 sec | 2.2 | |
| Extension | 72° C. | 30 sec | 4.4 | |
| Melt analysis | | Per Instrument Parameters | | |

Using 3 replicates of $C_p$ values per sample, per amplicon, a normalized Q-ratio was obtained with Equations 3 and 4.

$$Q \text{ ratio for genomic standard} = 2^{(average(Cp66) - average(Cp191))} \quad \text{(Eq. 3)}$$

$$Q \text{ ratio} = \times \frac{2^{(average(Cp66) - average(Cp191))}}{Q \text{ ratio for genomic standard}} \quad \text{(Eq. 4)}$$

Notably, the above approach offered the advantage of obviating the use of a standard curve as described to in Example 1. Instead, each sample is normalized to a single genomic standard (in this case, high quality genomic DNA). In one aspect, this approach can account for deviation in experimental variables, such as the day on which the experiment was run, the model of thermocycler, and the like. To determine DNA input for downstream sequencing, the normalized Q-ratio was used to determine the required input mass for each sample as follows according to Equation 5.

$$m_r = \frac{k_{Qm}}{Q \text{ ratio}} \quad \text{(Eq. 5)}$$

In this case, $m_r$ was the required input mass and the quality-mass constant ($k_{Qm}$) was set to a value of 10. Notably, the QUBIT dsDNA HS Assay Kit (THERMO FISHER) was used to quantify the DNA.

A next step of the method was the preparation of sequencing libraries. For UNG treatment, the required amount of extracted DNA was added into each tube, as described above. DNA was diluted with water to bring the total volume to 30.5 µL. The DNA polishing master mix was prepared as described in Table 7.

TABLE 7

DNA Polishing Master mix

| Reagent | Volume per reaction |
| --- | --- |
| 2 U/µL UNG Enzyme | 1 µl |
| KAPA Frag Buffer (10X) | 3.5 µl |

To each sample, 4.5 µL of DNA polishing master mix was added and then mixed by pipetting or vortexing. Samples were briefly centrifuged to settle the liquid to the bottom and then incubated in a thermocycler at 37° C. for 30 minutes. Immediately following incubation, samples were prepared for fragmentation. Sample tubes were placed on ice while setting up the fragmentation reaction master mix as detailed in Table 8.

TABLE 8

Fragmentation Master mix

| Reagent | Volume per reaction |
| --- | --- |
| KAPA Frag Buffer (10X) | 1.5 uL |
| KAPA Frag Enzyme | 10 uL |
| Nuclease-Free Water | 3.5 uL |

Notably, as the fragmentation master mix in Table 8 was highly viscous, necessitating the preparation of an excess total volume to ensure an adequate amount for use. To each sample, 15 µL of the fragmentation master mix was added on ice. Samples were mixed by vortexing and briefly centrifuged to settle the liquid to the bottom of the tubes. Samples were then incubated in a thermocycler at 37° C. for 30 minutes. At this point, samples were ready for A-tailing using, for example, the KAPA HyperPlus kit (ROCHE).

The schematic flow charts shown in the Figures are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the Figures are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention is presented in several varying embodiments in the following description with reference to the Figures, in which like numbers represent the same or similar elements. Reference throughout this specification to "one embodiment", "an embodiment", or similar language means that a particular feature, structure, or characteristic described in connection with the embodiment is included in at least one embodiment of the present invention. Thus, appearances of the phrases "in one embodiment", "in an embodiment", and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention. Accordingly, the foregoing description is meant to be exemplary, and does not limit the scope of present inventive concepts.

Each reference identified in the present application is herein incorporated by reference in its entirety.

What is claimed is:

1. A method comprising:
   (a) isolating DNA from a source, thereby providing a composition comprising the isolated DNA, wherein the isolated DNA has at least a first target region having a first length in nucleotides and a second target region having a second length in nucleotides, wherein the second length is greater than the first length, and the first target region and the second target region are a long interspersed nuclear element (LINE);
   (b) quantifying a total mass of the isolated DNA in the composition;
   (c) quantifying a first concentration of the first target region and a second concentration of the second target region in the composition;
   (d) calculating a Q-ratio for the isolated DNA by dividing the second concentration by the first concentration;
   (e) determining a value for a quality-mass constant ($k_{Qm}$) by a method comprising: (i) sequencing a plurality of regions of a plurality of isolated DNA samples, wherein each of the isolated DNA samples has a known input mass and a known Q-ratio; (ii) comparing a fraction ($F_D$) of the plurality of the regions with a selected depth of coverage as determined by sequencing in step (a) with a product of the input mass and the Q-ratio for each of the isolated DNA samples; (iii) identifying a minimum value for the product of the input mass and the Q-ratio at which $F_D$ is greater than a target $F_D$; and (iv) setting the quality-mass constant ($k_{Qm}$) equal to the minimum value for the product of the input mass and the Q-ratio determined in step (iii);
   (f) estimating a required input mass for the isolated DNA by dividing the quality-mass constant ($k_{Qm}$) by the Q-ratio; and
   (g) preparing the isolated DNA for sequencing if the total mass of the isolated DNA in the composition is equal or greater than the required input mass.

2. The method of claim 1, further comprising:
   (a) combining the isolated DNA composition with a uracil N-glycosylase (UNG) in a first buffer to provide a first mixture, wherein a portion of the isolated DNA composition includes at least one uracil moiety;
   (b) incubating the first mixture under conditions suitable to degrade the portion of the isolated DNA composition;
   (c) combining the first mixture with a dsDNA fragmentation enzyme to provide a second mixture; and
   (d) incubating the second mixture under conditions suitable to fragment the isolated DNA composition,
   wherein steps (b), (c), and (d) occur in the first buffer.

* * * * *

```
                        SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttgcggaagt cagtgtgg                                                  18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatggctggg tcaaatggta                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acttggaacc aacccaaatg                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgagaatatg cggtgtttgg                                                20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
      primer

<400> SEQUENCE: 5
caaacaaccc catcaaaaag tg                                                22
```